(12) United States Patent
Huiku et al.

(10) Patent No.: US 7,407,486 B2
(45) Date of Patent: Aug. 5, 2008

(54) METHOD AND AN APPARATUS FOR PULSE PLETHYSMOGRAPH BASED DETECTION OF NOCICEPTION DURING ANESTHESIA OR SEDATION

(75) Inventors: Matti Veli Tapani Huiku, Espoo (FI); Ilkka Korhonen, Lempäälä (FI); Marcus Johannis Van Gils, Tampere (FI); Mikko Oskari Jousi, Helsinki (FI); Jyrki Mika Petteri Lötjönen, Valkeakoski (FI)

(73) Assignee: GE Healthcare Finland Oy (FI)

( * ) Notice: Subject to any disclaimer, the term of this patent is extended or adjusted under 35 U.S.C. 154(b) by 223 days.

(21) Appl. No.: 10/474,786

(22) PCT Filed: Oct. 14, 2002

(86) PCT No.: PCT/IB02/04201

§ 371 (c)(1),
(2), (4) Date: Mar. 2, 2005

(87) PCT Pub. No.: WO2004/034897

PCT Pub. Date: Apr. 29, 2004

(65) Prior Publication Data

US 2005/0143665 A1 Jun. 30, 2005

(51) Int. Cl.
*A61B 5/02* (2006.01)
(52) U.S. Cl. .................................... 600/500; 600/481
(58) Field of Classification Search ................ 600/481, 600/500
See application file for complete search history.

(56) References Cited

U.S. PATENT DOCUMENTS 3,734,086 A * 5/1973 Phelps, Sr. .................. 600/500
5,871,450 A * 2/1999 Nomura et al. ............. 600/485
6,048,318 A * 4/2000 Chesney et al. ............. 600/483

(Continued)

FOREIGN PATENT DOCUMENTS

EP  0 774 234  5/1997

OTHER PUBLICATIONS

*The Peripheral Pulse Wave: Information Overlooked*, Willie B. Murray and Patrick A. Foster, Journal of Clinical Monitoring, vol. 12, pp. 365-377, 1996.

(Continued)

*Primary Examiner*—Robert L. Nasser, Jr.
*Assistant Examiner*—Karen E Toth
(74) *Attorney, Agent, or Firm*—Andrus, Sceales, Starke & Sawall, LLP (57) ABSTRACT

The invention concerns a method and an apparatus for monitoring a condition of a patient under anesthesia or sedation. For this purpose there is a sensor for acquiring a signal that represents peripheral cardiovascular flow in the patient. Successive heart beat pulses are detected and predetermined pulse wave parameters are measured repeatedly in said signal, and predefined pulse wave parameters within said heart beat pulses are measured, too. At first, said predetermined pulse wave parameters in a number of successive heart beat pulses are compared in respect to possible occurrence of a substantial alteration. At second, if the alteration is noticed, a statistical reference value is calculated by deriving values from at least said predefined pulse wave parameters, and the change(s) between at least one predefined pulse wave parameter and said reference value is quantified. The results and/or intermediate results are finally displayed and/or recorded.

32 Claims, 6 Drawing Sheets

U.S. PATENT DOCUMENTS

| | | | |
|---|---|---|---|
| 6,117,075 A | 9/2000 | Barnea | |
| 6,120,443 A | 9/2000 | Cohen-Laroque | |
| 6,315,736 B1 * | 11/2001 | Tsutsumi et al. | 600/500 |
| 6,322,515 B1 * | 11/2001 | Goor et al. | 600/485 |
| 6,702,752 B2 * | 3/2004 | Dekker | 600/484 |
| 6,932,772 B2 * | 8/2005 | Kan | 600/490 |
| 2002/0095092 A1 * | 7/2002 | Kondo et al. | 600/503 |
| 2002/0161304 A1 * | 10/2002 | Eide | 600/485 |
| 2004/0015091 A1 * | 1/2004 | Greenwald et al. | 600/513 |

OTHER PUBLICATIONS

European Search Report in corresponding European Patent Application No. 02772738.7 dated Aug. 28, 2007.

"The difference in pulse transit time to the toe and finger measured by photoplethysmography", Institute of Physics Publishing; Physiol. Meas. 23 (2002) 85-93.

* cited by examiner

METHOD AND AN APPARATUS FOR PULSE PLETHYSMOGRAPH BASED DETECTION OF NOCICEPTION DURING ANESTHESIA OR SEDATION

CROSS REFERENCE TO RELATED APPLICATION

The present application is the U.S. national stage application of International Application PCT/IB02/04201, filed Oct. 14, 2002, which international application was published on Apr. 29, 2004 under International Publication No. WO 2004/034897.

The present invention relates to a method for determining the adequacy of analgesia in anesthetized or sedated subjects and, in particular, relates to a specific usage of e.g. plethysmographic pulses as an indicator for the level of analgesia and nociception during anesthesia.

Concept of the depth of anesthesia has been of interest for recent decades, and several measures have been proposed to assess the depth of anesthesia. Recently, however, this unitary anesthesia theory of the existence of one-dimensional concept called "depth of anesthesia" has been strongly criticized as oversimplified. Instead it has been suggested that the anesthesia has not one but three main components: hypnosis, analgesia and muscle relaxation. Different anesthetic regimens have different effect on these three components. Furthermore, they have effects on both cortical and sub-cortical levels. An adequate anesthesia means unresponsiveness to both noxious and non-noxious stimuli. The former may be defined by means of hemodynamic, motor and endocrine stability, while the latter is related to the loss of consciousness and recall and amnesia. In practice the adequate anesthesia is administered by using a combination of drugs with different effects on brain, spinal cord, autonomic nervous system and neuro-muscular junction. The combination of these effects hence creates the hypnotic, analgesic and muscle relaxing effects.

In general anesthesia the patient is conducted through the phases of anesthesia from the induction to the varying lengths of maintenance period and to the final emergence out from anesthesia. Though the patient does not usually recall any surgical events or perceive surgical pain, the recovery and the post-operative comfort of the patient very often depend on the quality of the anesthesia during the operation itself. Adequate administration of analgesic drugs—meaning that over-doses and under-doses can be avoided during anesthesia—is believed to advance the recovery of the patient. It has been suggested that this is due to two main reasons. Surgical pain may sensitize the pain pathways during surgery and thus lower the pain threshold in such a way that even rather intense pain management in the post-operative period is ineffective. It is said that the best way to avoid post-operative pain is a good and adequate administration of analgesics during operation. The other mechanism is probably related to the secretions of stress hormones during surgery. These hormones may have their effects long after surgery and can slow down the physical and psycho-physiological heeling of the patient. Adequate pain medications can suppress the autonomic nervous system and prevent excess secretion of these stress hormones. In this context the term "nociception" is commonly used to refer to the perception of pain. The receptors involved in pain detection are aptly enough referred to as nociceptors. Nociceptive input is conveyed from the peripheral end organs to the central nervous system. Projection neurons in the spinal dorsal horn project to cell nuclei in supraspinal areas such as the thalamus, the brainstem, the midbrain etc. Of these, the synaptic junctions in the thalamus play a very important role in the integration and modulation of spinal nociceptive and non-nociceptive inputs. Nociceptive inputs are finally conducted to the cortex, where the sensation of pain is perceived. Stimulation of these brain regions either electrically or chemically, e.g. by morphine and other opiates, produces analgesia in humans.

Currently the anesthesia practices rely on rather subjective assessments of the adequacy of the drug treatment during anesthesia. Anesthesiologists observe the patient and decide for the proper drugs they give to the patient. Though this often is enough to avoid adverse events such as arousal or muscle movements during surgery, which in fact very seldom occur in normal anesthesia nowadays, more objective measures for the anesthesia are needed. Recently the progress in the EEG signal analysis has lead in reasonable quantitative estimation of the hypnotic level of the patient, and thereby the titration of the anesthetic agents can be guided by these new measurements. The administration of analgetics, however, is still based on the visual observations of the vital signs and the hemodynamic responses of the patient to surgical stimulation. Analgesic drugs are usually given, when the heart rate or blood pressure show fast increases or are in long term at the high end of the normal ranges. Different motoric responses, sweating and lacrimation of the patient can be observed as well.

Another way is to observe a photoplethysmographic (=PPG) signal, which is obtained by measuring the intensity of light transmitted through or reflected by the tissue. The dynamic part of the signal is caused by variations in blood volume and perfusion of the tissue, affecting scattering and absorption of the incident light. The most usual application of the signal is the measurement of the oxygen saturation of blood. The pulse waveform of the PPG signal is closely similar to that of the intraarterial blood pressure. The waveform is reflecting the interaction between left ventricular output, i.e. cardiac output or stroke volume, and the capacitance of the vascular tree, also called vascular resistance. Blood pressure is determined by the cardiac output, which is stroke volume multiplied by heart rate, and vascular resistance. However, in addition to these global circulatory parameters, the dynamic capacitance of the vasculature affects also the nonlinear relationship of PPG signal and circulatory parameters. Especially complex is the relationship between the PPG waveform shape within one pulse and the integrated pulse-to-pulse variables. The PPG signal is related to the changes in peripheral tissue blood volume and blood absorptivity. As it is the blood flow, that causes the blood volume changes, the PPG signal is hence indirectly related to local blood flow. The flow, in turn, depends on the pressure gradient and local vascular dynamic resistance and capacitance.

Figure 2:
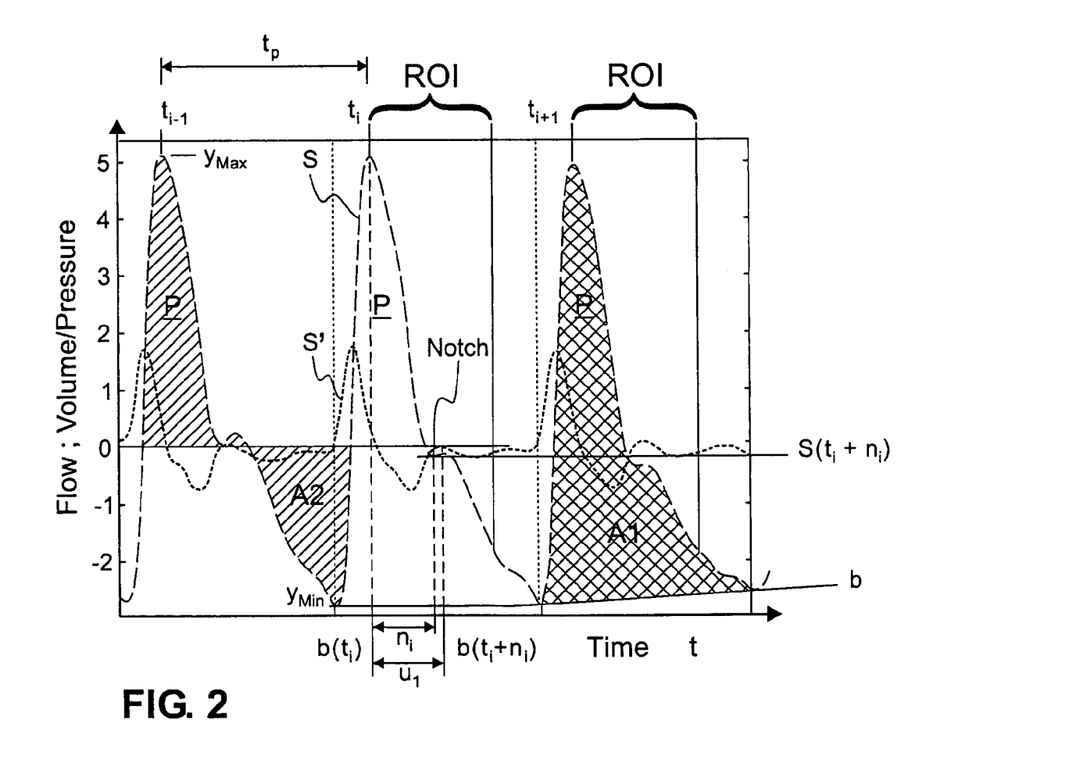
FIG. 2 shows an example of a typical signal, like PPG signal, representing peripheral cardiovascular flow in the patients, by dashed line, which signal is used for the invention, and the derivative of the same signal by dotted line, as well as the functional components of the signal for detecting and for determining the morphology of the pulse wave.
Figure 3:
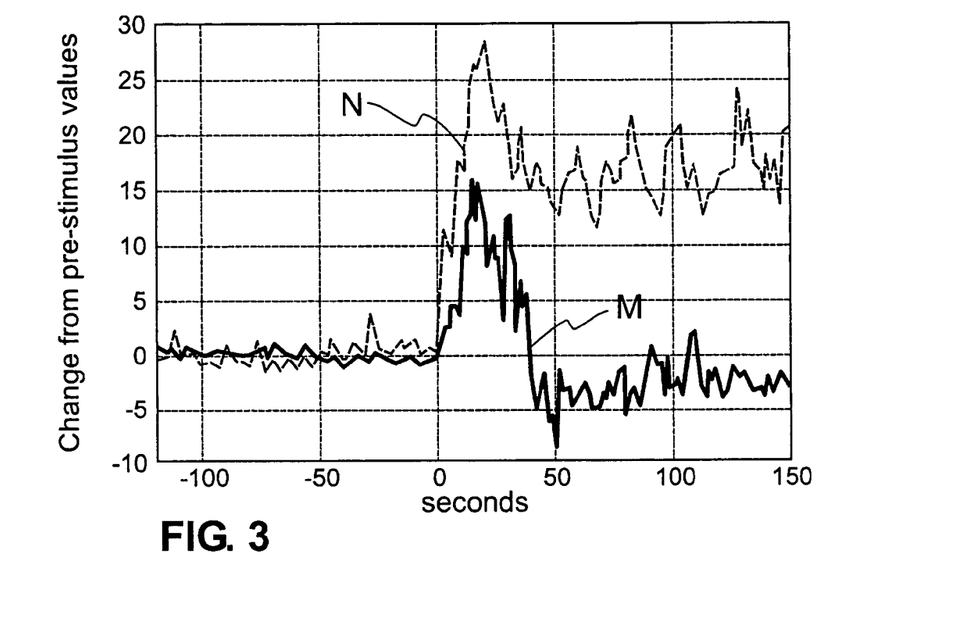
FIG. 3 shows the relative average signal value of the PPG notch level as a mean response to incision from patients who reacted (=M) to the incision during anesthesia and from patients who did not reacted (=N) to the incision during anesthesia respectively. Time=0 means the incident of the incision. The curves are normalized in respect to pre-incision notch level, in respect to beat-to-beat maximum pulse amplitudes, in respect to basal PPG signal level and in respect to heart rate.

A typical PPG waveform is depicted in FIG. 2. The amplitude of the signal increases during systole and decreases during diastole run-off. The steepness of the curve in the rising edge is related to the force of the ventricular contraction while the amplitude is related to the stroke volume. However, these are also modified by other factors including e.g. local vascular capacitance and blood pressure, and so only relative changes may be correlated to each other. In the descending phase of the curve appears the dicrotic notch, which is classically, in the analysis of blood pressure waveforms, attributed to the closure of the aortic valve at the end of the ventricular systole and the pulse pressure wave reflections in the vasculature. However, it is questionable whether this interpretation may be used for the PPG waveform. It has been suggested that the vertical position of the dicrotic notch would be an indicator of the vasomotor tone. In most circumstances the notch descends to the baseline during increasing vasodilatation and climbs towards the apex with vasoconstriction. The interpretation of the dicrotic notch requires comparison of successive beats. Only few studies have been published on the topic, and therefore, the interpretations should be considered speculative. Circulation is controlled by autonomic nervous system. Especially sympathetic activation to the heart causes heart rate acceleration and an increase in blood pressure through vasoconstriction. Sudden pain causes a stress reaction, which is associated with sympathetic activation leading to sudden increase in heart rate (=HR) and blood pressure. Hence, in clinical practice HR and blood pressure responses have been used for decades by experienced anesthesiologists to heuristically detect inadequacy of anesthesia. However, not only pain but also various other issues may cause variations in HR and blood pressure, and consequently the HR and blood pressure are continuously varying. Hence, monitoring just the mean level of HR and blood pressure is not sufficient.

The PPG measuring as such has been utilized for a long time. For instance publication U.S. Pat. No. 6,117,075 discloses a method and device for monitoring the depth of anesthesia (=DOA) during surgery by analyzing patterns and characteristics of oscillatory phenomena in measured pulse pressure and skin temperature signals. The method utilizes pulse pressure and skin temperature oscillatory patterns describe the nature of sympathetic vasomotor tone. The method monitors DOA in two ways. Spectral characteristics of skin temperature or pulse pressure oscillatory phenomena are used to describe the depth of anesthesia, and the concordance between oscillatory patterns of two physiological signals, which have been recorded simultaneously but at different locations, are used to describe the depth of anesthesia. According to the publication a PPG signal of an anesthetized patient is continuously monitored, and the recorded raw PPG signal is then processed so as to generate a signal depicting the beat-to-beat pulse pressure amplitude. Then a signal is derived by detecting peaks, and calculating the difference between each positive-negative peak pair, after which a further signal is processed in a manner so as to derive a data set describing very low frequency variations in pulse pressure over time in the 0.01-0.04 Hz range, that is, the PPG signal amplitude variability. Power spectrum analysis is finally performed on said further signal, and the received frequency power spectrum characteristics are used to describe the DOA, such that a progressively narrower bandwidth describe a progressively deeper level of anesthesia.

The publication *Journal of Clinical Monitoring* 12: W. B. Murray, P. A. Foster—The Peripheral Pulse Wave: Information Overlooked; 365-377, 1996 suggests that the amplitude of the PPG signal as well as the position of the dicrotic notch would be sensitive indicators of the level of catecholamine stimulation. They suggest that decrease in the amplitude of the dicrotic notch associated with elevation of the dicrotic notch would be an early indicator of the lightening anesthesia. They also suggest that vasodilation would be associated with decrease in the relative position of the dicrotic notch in the baseline. However, it appears that the position of the dicrotic notch as well as the PPG amplitude are dependent on various other sources than the status of vasoconstriction or vasodilatation, including fluid balance, temperature of the site of PPG measurement, heart rate, etc. Hence, these parameters may be interpreted with caution. Furthermore, they refer to the usage of the PPG information as a measure of the depth of anesthesia, which is an oversimplified one-dimensional assumption as described above.

The main object of the invention is to achieve a method for monitoring the anesthesia or sedation of a patient so that a reliable data about level or depth of analgesia would be available to an anesthetist or to other purposes. The second object of the invention is to achieve a method for monitoring the anesthesia or sedation capable of using measured signals derived from various sources of the patient, which means that the method should not be dependent on any single type of detector. The third object of the invention is to achieve a method for monitoring the anesthesia or sedation capable to deliver such results as an output, with the basis of which the adequacy of analgesia could be reliably enough assessed by inexperienced anesthetists or other operators, too. The fourth object of the invention is to achieve a method for monitoring the anesthesia or sedation functioning with an acceptable speed so that a change in analgesia to a hazardous direction is detected and reported early enough to allow timely corrective actions. A further object of the invention is to detect impending nociception, if only possible prior to a certain level of nociception arouses, to avoid possible long-term traumas and/or syndromes of maintained pain.

The above-described problems can be solved and the above-defined objects can be achieved by the inventive method. The current invention relates to the specific usage of cardiovascular flow pulse morphology as an indicator for the level of analgesia and nociception during anesthesia, which is different from the concept of the depth of anesthesia, which mainly relates to the hypnotic component of anesthesia.

According to the first aspect of the invention the method for monitoring a condition of a patient under anesthesia or sedation, comprises the steps of: acquiring a signal representing peripheral cardiovascular flow in the patient; detecting individual heart beat pulses in said signal; measuring predetermined pulse wave parameters of said signal at least within said individual heart beat pulses; repeating the measuring of said pulse wave parameters in the successive heart beat pulses. The method further comprises the steps of: recording said measured pulse wave parameters; calculating a reference value over a predetermined time period or over a predetermined number of heart beat pulses by deriving values of at least one predefined pulse wave parameter from said recorded pulse wave parameters; quantifying change(s) between one or several prevailing predefined pulse wave parameter(s) and said reference value; and displaying and/or recording said change(s) in said at least one pulse wave parameter.

According to the second aspect of the invention the method for monitoring a condition of a patient under anesthesia or sedation, comprises the steps of: acquiring a signal representing peripheral cardiovascular flow in the patient; detecting successive heart beat pulses in said signal; measuring predetermined pulse wave parameters repeatedly in said signal at least within said successive heart beat pulses. The method further comprises the steps of: measuring predefined pulse wave parameters within said heart beat pulses; comparing said predetermined pulse wave parameters in a number of successive heart beat pulses, and if a substantial alteration is occurred, calculating a statistical reference value by deriving values at least from said predefined pulse wave parameters, quantifying change(s) between at least one predefined pulse wave parameter and said reference value; and displaying and/or recording said change(s) or lack of change(s) respectively in said at least one predefined pulse wave parameter.

According to the third aspect of the invention the apparatus for monitoring a condition of a patient under anaesthesia or sedation comprises: sensor means for receiving a substantially continuous electrical signal representing a cardiovascular flow of the patient; time measuring means and a voltage/ current dependent circuit connected with said sensor means. The apparatus further comprises: first memory means storing criteria of predetermined pulse wave parameter(s); first calculation means and/or selection means connected to said first memory means, said time measuring means and said voltage/current dependent circuit for detecting predefined pulse wave parameter(s) of said predetermined pulse wave parameter(s) in said signal; quantifying means providing quantified change(s) of at least one predefined pulse wave parameter in respect to values of said predefined pulse wave parameter prior to the present moment; and a display and/or connections into other possible devices.

The invention and its preferred embodiments are now described more in detail with reference made to the accompanying drawings.

FIG. 6A a clear dicrotic notch can be seen, and in FIG. 6B a virtual dicrotic notch can be seen, both being feasible for the morphological analysis according to the invention. Lack of nociception can be evidenced for patient of FIG. 6A, while the notch signal level after incision is higher than the preceding average thereof. Presence of nociception can be evidenced for patient of FIG. 6B, while the notch signal level after incision is lower than the preceding average thereof.

FIGS. 9A to 9D show a case, in which a healthy volunteer is deeply sedated with propofol. A heart rate R-to-R interval (=RRI) in FIG. 9A, systemic arterial pressure (=SAP) in FIG. 9B, and pulse wave plethysmograph (=PPG) signals were recorded from the subject. From PPG signal, pulse amplitude, FIG. 9C, and relative vertical notch position, FIG. 9D, were derived and plotted on beat-to-beat scale.

Figure 1:
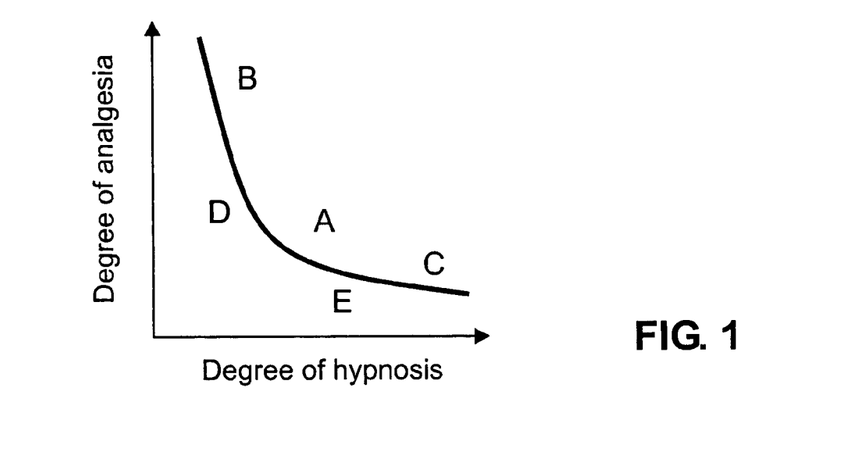
FIG. 1 describes the principle of interdependency between hypnosis and analgesia, whereupon the adequacy of another is dependent of the degree of the other.

The present innovation proposes a method, which enables monitoring condition of a patient under anesthesia or sedation, and specifically enables to assess the adequacy of analgesia in anaesthetized or sedated subjects in real time, based on the measurement of sympathetic reactions in beat-to-beat PPG time series. In anesthesia there is a need to assess level of analgesia i.e. adequacy of pain medication, in order to avoid the subject to feel pain during the operation. This is a complicated task in presence of other medication, such as hypnotic agents and especially muscle relaxants. The invention functions successfully in solving this task and so fills the missing link in the complete anesthesia monitoring. Especially for analgesia and hypnosis, the adequacy of another is dependent on the level of the other one as schematically shown in FIG. 1. In area D the degree or level of analgesia is acceptable as such, but the degree or level of hypnosis is quite too low, which case corresponds a local analgesia or anesthesia and is not practical or acceptable in many cases. In area E the degree of hypnosis is acceptable as such but the degree of analgesia is quite too low, whereupon the patient does not have consciousness during operation and does not remember anything about the operation afterwards, but the pain of the operation cause traumatic symptoms anyway. In area B the degree of analgesia is high enough so that a lower degree of hypnosis can be utilized, and in area C the degree of hypnosis is high enough so that a lower degree of analgesia can be utilized. In area A both the analgesia and the hypnosis has optimal levels, but generally points on the right hand side of the curve in FIG. 1 are useful and points on the left hand side of the curve shall be avoided during general anesthesia. For optimal general anesthesia all the three components, which are analgesia, hypnosis and muscle relaxation should be controlled. This requires methods to independently assess all the components. This innovation is based on the facts that pain causes sympathetic activation. Sympathetic activation propagates via sympathetic nervous branches to different sites of the body, including heart and blood vessels. In the blood vessels the activation causes vasoconstriction and increases hence blood pressure. In the heart sympathetic activation causes heart rate acceleration.

Figure 4:
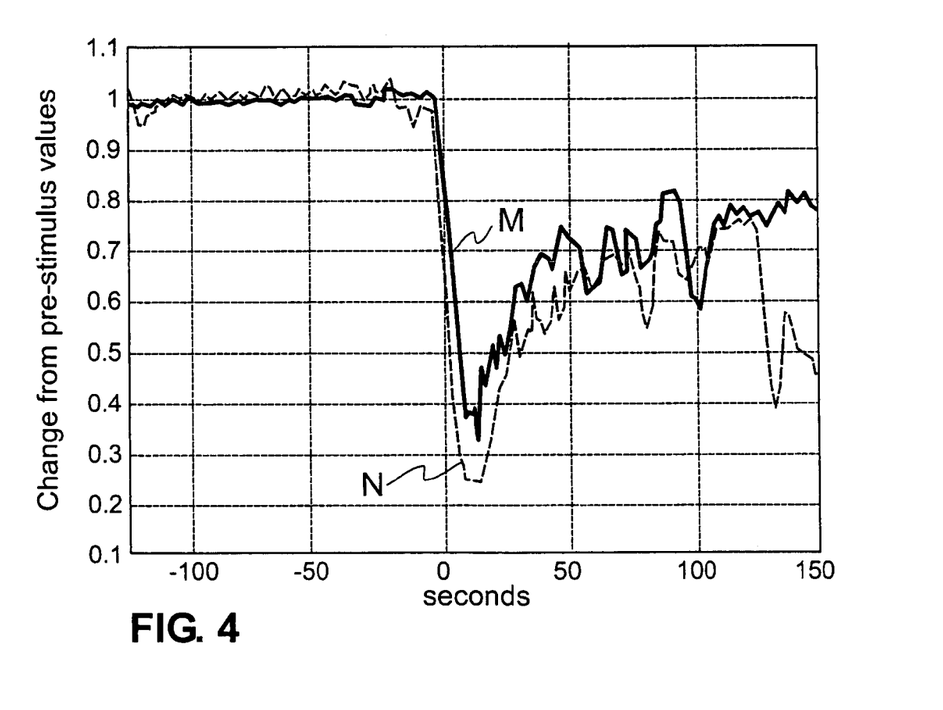
FIG. 4 shows the relative average value of the PPG maximum pulse amplitude as a response to incision from patients who reacted (=M) to the incision during anesthesia and from patients who did not reacted (=N) to the incision during anesthesia respectively. Time=0 means the incident of the incision. The curves are normalized in respect to pre-incision maximum pulse amplitudes and in respect to heart rate.

The pulse amplitude of the PPG signal S is known to decrease as a response to noxious stimulus. However, this measure as itself does not provide a proper quantification of an adequacy of analgesia, because the response is similar to both submaximal stimulus and supramaximal stimulus. In general supramaximal stimulus means "stronger than the highest possible nerve stimulation", and so in this case a state, in which an activation of the nociceptors, i.e. a nociceptive input exceeds the transduction capacity of the afferent fibers, whereupon it is ensured that signaling nociception is on its maximum. Submaximal stimulus means "less than the highest possible nerve stimulation", and so in this case a state, in which a further activation of the nociceptors causes increased transduction in the afferent fibers and a stronger response. There is no clear and measurable difference between patients, who respond M to incision during anesthesia or sedation and those, who does not respond N to incision during anesthesia or sedation, as shown in FIG. 4. Surprisingly, it has now noticed that at least the vertical location of the dicrotic notch in the PPG signal carries unique information related to the nociception during anesthesia. The PPG notch response to a nociceptive stimulus is related to the perceived nociception, i.e. there is a significant difference in the response depending on whether the nociception has been submaximal or supramaximal.

Healthy volunteers during light sedation or analgesia was examined, and heart rate like R-to-R interval, or a reciprocal of heart rate, and systemic arterial pressure and pulse wave photoplethysmograph (=PPG) signals were recorded from the volunteers. From the PPG signal, pulse amplitude and relative vertical notch position were derived and plotted on beat-to-beat scale. An electrical nociceptive stimulus was delivered to the volunteers, while the volunteers were slightly or deeply sedated (Ramsay scores 3 and 4) with propofol. As a response to electrical nociceptive stimulation there is an increase in SAP and decrease in PPG amplitude and notch relative level. However, there are also other variations in SAP and PPG amplitude prior to stimulus, and only PPG notch drop appears as a specific marker for nociception, as shown in FIGS. 9A-9D. The PPG amplitude appears to follow mainly changes in SAP and is not specific for nociception, but the PPG notch appears as a specific marker for nociception.

The present invention utilizes this as follows. The PPG notch position together with PPG pulse amplitude and other vital signs are used to monitor nociception during anesthesia. The PPG amplitude and especially sudden drops in the amplitude, possibly but not necessarily accompanied with characteristic changes in other vital signs, provides a nonspecific marker for potential nociception. If such characteristics are observed in these signals, the PPG notch position is checked and if the characteristics of the PPG notch curve change, as is typical during nociception, nociception of the patient is evidenced. The PPG notch vertical position, i.e. the amplitude thereof, may be monitored also separately to provide information about the nociceptive status of the patient. The monitoring of the PPG notch position is implemented in a monitoring apparatus, consisting of means for measuring the PPG signal, detecting PPG pulse waveforms, and identifying the PPG notch in each pulse wave. Extracted information may be provided in a beat-to-beat representation or as filtered over several beats. The PPG amplitude as well as the pulse morphology, including position of the dicrotic notch, are dependent on various factors, including vasodilation and vasoconstriction, heart rate, blood pressure, fluid balance, measurement site temperature, etc. As these factors may vary during operation largely, as well as between the individuals, normalization of the signal should be carried out, and focus should be laid on normalized signals. The normalization, i.e. equalizing and proportionating described later in detail, aims to compensate these long-term variations as well as inter-individual differences in order to detect nociception and hence insufficient analgesia during anesthesia or sedation.

The method concerns monitoring a condition of a patient under anesthesia or sedation, which is a complicated situation in the sense that the patient is not able to tell his/her feelings like smart or pain, contrary to normal situation under consciousness. In principle this method of the monitoring can be utilized for determining an adequacy of analgesia in any circumstances, whereupon the patient, a human or an animal, either can be conscious/awake, i.e. not under hypnosis, or can be unconscious, i.e. under anesthesia or sedation. In practice the method provides substantial advantages in cases the human patient is not able to communicate normally. For this purpose the method comprises the following steps. At first a signal S representing peripheral cardiovascular flow in the patient is acquired. This acquiring can be preferably performed using e.g. a photoplethysmographic unit, whereupon a PPG pulse wave signal, or a signal dependent on blood volume and/or a signal dependent on blood pressure is received. The raw signal is received from sensor means 15, like a pulse oximeter sensor or a pneumatic continuous blood pressure meter, and then typically processed in signal conditioning means 18, which controls and adjusts the raw signal e.g. by amplifying, offset-removing, filtering etc. to a proper level and quality for the following steps. The peripheral blood flow in itself is difficult to measure, but the sensors typically give a signal, which is dependent on either the blood pressure or the blood volume or both in the peripheral part of the body. The peripheral part of the body of the patient, in which the sensor is positioned, is practically a finger, a toe, or earlap, or a respective area. The sensors in question can be of any known or new type detecting indirectly the flow, pressure or volume of the blood without any direct contact with the blood, and so they are not described in detail. The sensor 15 so gives a substantially continuous electrical signal S for further processing.

Next the individual heart beat pulses P in said signal are detected from the substantially continuous electrical signal S. The heart beat pulses extend from each point of minimum basal signal value $y_{Min}$ to the next point of minimum basal signal value, whereupon there is a peak amplitude $y_{Max}$ between these two minimum values. The minimum basal signal value $y_{Min}$ and the peak amplitude $y_{Max}$ are detected by a voltage/current dependent circuit 6 connected to said sensor means 15.

Then predetermined pulse wave parameters of said signal at least within said individual heart beat pulses P are measured, and the measuring of the predetermined pulse wave parameters in the successive heart beat pulses is repeated for each successive heart beat pulses P. According to the invention the predetermined pulse wave parameters mentioned above are one or several parameter(s) selected from the following list of parameters: Peak amplitude(s) $y_{Max}$ within said individual heart beat pulse(s) P, i.e. between each successive minimum basal signal values; temporal position(s) $t_i$ of said peak amplitude(s); minimum basal signal value(s) $y_{Min}$ between said heart beat pulse(s), i.e. between each successive peak amplitudes; dicrotic notch signal value(s) s within said individual heart beat pulses, more specifically between the peak amplitude and the next minimum basal signal value; temporal position(s) $n_t$ of said dicrotic notch value(s), and pulse beat period(s) $t_P$ between said heart beat pulses, and pulse area(s) A1 of said heart beat pulse(s), and area(s) A2 under curve(s) of said heart beat pulse(s) and measuring baseline fluctuations of the PPG signal. Some of the pulse wave parameters can be directly detected or selected from the voltage/current circuit 6 and the time measuring means 5 using the selection means 8, whereupon the selecting criteria for the purpose are stored in the first memory means 11, but some of the pulse wave parameters shall be calculated using the data derived from the signal S. This can be performed by the first calculation means 1 using a proper algorithm, i.e. criteria for calculating those predetermined pulse wave parameters, which cannot be measured in a straight forward way from the signal S, which algorithm is also stored in the first memory means 11 of the apparatus. The voltage/current dependent circuit 6, the time measuring means 5 and the algorithm can be of any known or new type and are so not described in detail. Both the directly measured and calculated parameters, are recorded or stored in the second memory means 12 at least temporarily for availability in the following calculations. In general here, notes t and x refer to time, i.e.

horizontal axis, and notes y and N refer to magnitude and the vertical axis in the perpendicular system of coordinates.

Figure 5:
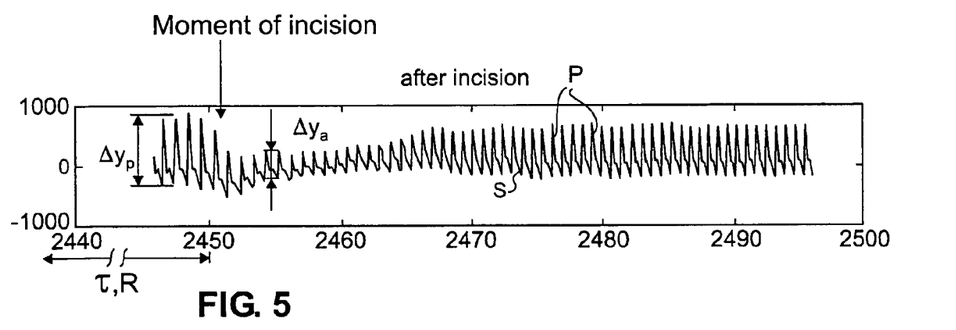
FIG. 5 shows a typical PPG signal prior to and after an incision, a change in the heart rate and in the pulse amplitude caused by the nociception being visible.

It is believed that, according to the invention, the most reliable results can be attained by proceeding through at least the three following steps, though results with lower reliability could possibly be attained using fewer or modified steps. So, the preferred embodiment of the method of the invention has a first step, in which a possible suppression of at least one of the wave parameters is detected in their absolute value scale. For instance FIG. 5 show suppression of pulse amplitude, the amplitude having a higher value $\Delta y_P$ prior to an incision and a smaller value $\Delta y_A$ after the incision, and accordingly a change $\Delta y_P - \Delta y_A$ of pulse amplitude. In case there is a suppression larger than a predetermined amount, i.e. the suppression $\Delta y_P - \Delta y_A$ exceeds a certain second predetermined threshold value stored in the third memory means 13 of the apparatus, the second step is initiated, and the quantified change(s) for the results and/or optional evaluation of the results, which are described later in detail, are deemed or considered to be valid. It is possible that analogous changes in other parameters can also be utilized for this pre-evaluation step.

Figure 6A:
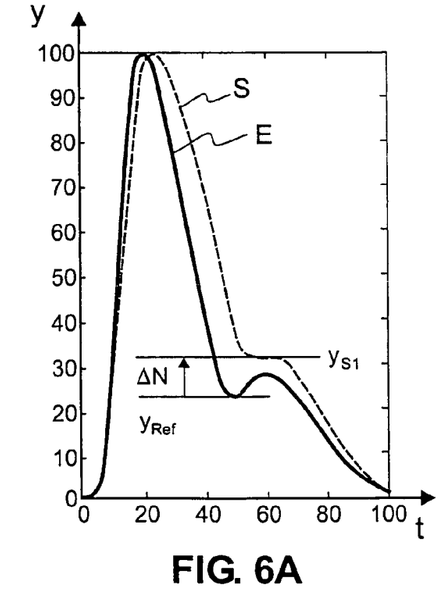
FIGS. 6A and 6B show examples of two individual heart beat pulses each derived from an equalized and proportionated signal representing peripheral cardiovascular flow in a single patient. The calculated average pulse shown by solid line E describes condition prior to incision, and the pulse signal shown by dotted line S describes condition after incision.
Figure 6B:
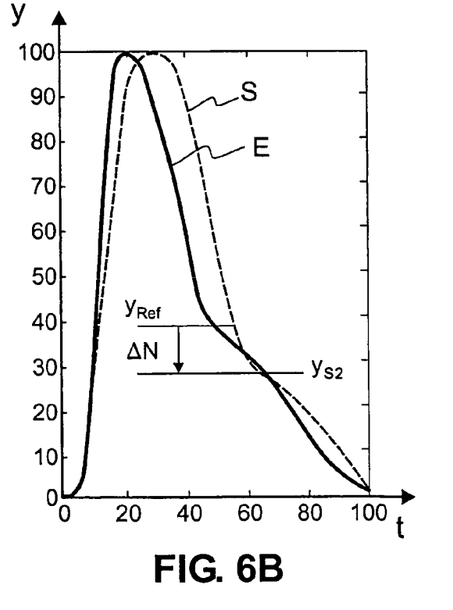
Figure 7:
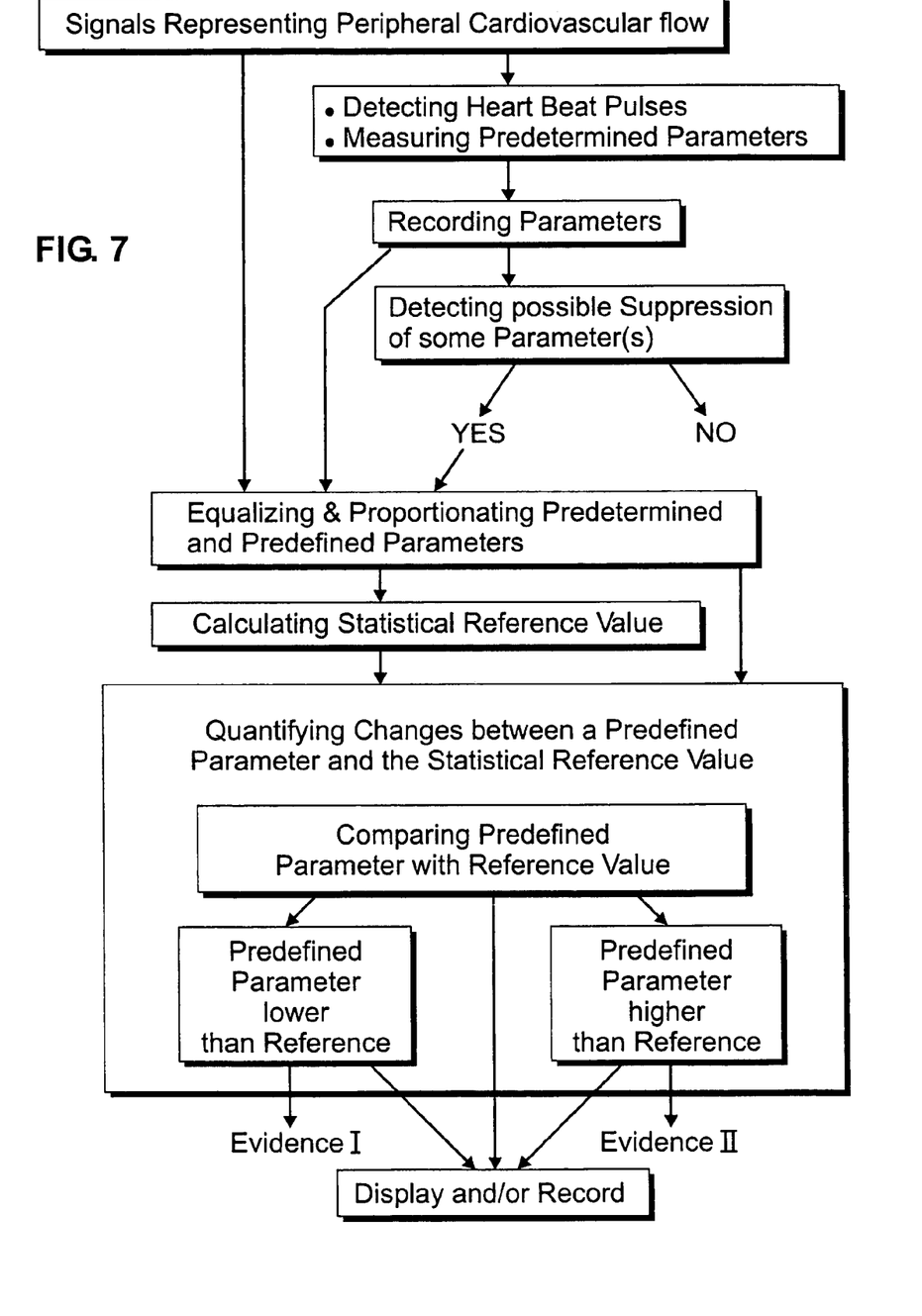
FIG. 7 shows the main steps of the preferred embodiment of the invention for processing or calculating the data derived from the heart beat pulses for attaining the results, which can be displayed and/or recorded and evaluated in respect to whether the patient suffers nociception or not. The combination of steps is repeated for each successive heart beat pulses.

In the second step, initiated after the first step if the predetermined change in the absolute value scale was found, the change of the shape in the pulse is detected, i.e. morphological analysis is performed. Preferably this analysis can be performed e.g. by scaling the parameters, by calculating a reference value $y_{Ref}$, and by quantifying change(s) x, y between one or several prevailing predefined pulse wave parameter(s) and said reference value. The mentioned predefined pulse wave parameter is, according to the invention, at least and preferably dicrotic notch signal value(s) $y_{S1}$ or virtual signal value(s) $y_{S2}$ approaching dicrotic notch respectively, within successive heart beat pulses. It can be also possible to use some other point within the descending side of the heart beat pulse, if the respective temporal positions thereof in the successive pulses could be determined. The scaling means equalizing said pulse wave parameter(s) within pulse beat period(s), and proportionating said measured dicrotic notch signal value(s) and temporal position(s) thereof, and the calculated notch reference value(s) and temporal position(s) thereof to respect said equalized region of parameter(s) and period(s). Shortly said this is stretching or compressing of each pulse signal to match the same signal amplitude and pulse period, the intermittent values of the pulse signal in proportion, as shown in FIGS. 6A and 6B. The reference value $y_{Ref}$ is calculated over a predetermined time period $\tau$ or over a predetermined number R of heart beat pulses by deriving values of at least one predefined pulse wave parameter from the pulse wave parameters recorded in the second memory means 12. Said reference value $y_{Ref}$ is calculated specifically for the patient under anesthesia or sedation; and that said reference value is a constant average value over said time period $\tau$ or over said number R of heart beat pulses prior to the present measuring time, e.g. prior to an incision, or a moving weighted or non-weighted average value over said time period $\tau$ or over said number R of heart beat pulses during operation of the patient, or a constant group average over certain patient type(s). The quantifying of change(s) x, y can be simply comparing the dicrotic notch signal value $y_{S1}$ or $y_{S2}$ in respect to the reference value $y_{Ref}$, a difference $\Delta N$ therebetween describing the morphological change in the pulse P.

The position of the actual and virtual notch can be detected e.g. as follows, whereupon the following notations are used:
s signal value
s' the first derivative of the signal value s
$t_i$ the time of the maximum of the signal for a single pulse beat i
$u_k$ the time index of the $k^{th}$ maximum of the first derivative s' in ROI
$n_i$ the time index of the notch of the pulse beat i in ROI
$s(t_i)$ the signal value at $t_i$ (local maximum)

The notch detection algorithm consists of the following steps: For each plethysmographic pulse i do:
Define the region-of-interest (ROI) between the value $r_1$ and $r_2$, where $r_1 = t_i$ and $r_2 = r_1 + W \times (t_{i+1} - t_i)$, and W is a user defined window width (e.g. W=60%).
Within ROI detect all local maxima of the time derivative of the signal s'. The time indices of the maxima, relative to the beginning of the ROI, are denoted by $u_k$ (k=1, 2, ...), i.e. u=0 at $r_1$
According to a predetermined notch detection strategy determine the most probable notch candidate k.
If $s'(u_k) > 0$, the notch is located at time index ni at the previous local minimum of the signal s just before the index $u_k$.
If $s'(u_k) \leq 0$, the notch is located at $n_i = u_k$, whereupon the relative notch position is determined in the following way:
Calculate the baseline of the signal, b, inside the ROI.
Compute the relative y-position of the notch at ni relative to the plethysmographic peak i at $t_i$: $y_i = (s(t_i + n_i) - b(t_i + n_i))/(s(t_i) - b(t_i))$
Compute the relative x-position of the notch at ni relative to the period of the plethysmographic pulse i: $x_i = n_i/(t_{i+1} - t_i)$.
Determine the change of the morphology of the pleth signal by calculating, $y = y_i - y_{Ref}$ and $x = x_i - x_{Ref}$, in which $y_{Ref}$ and $x_{Ref}$ are reference values.
Update the new reference values as: $y_{Ref} = y_{Ref} + f \times (y_i - y_{Ref})$ and $x_{Ref} = x_{Ref} + f \times (x_i - x_{Ref})$, where f is a user-specified constant (here f=0.2).

In many cases, the signal contains two possible notch positions. The confidence value strategy at the high vertical notch position favors the selection of the second peak, if the notch is not too close to signal baseline and the peak position does not differ too much from previous positions.

The equalizing and proportionating of the pulse wave parameter(s) may be carried out in various ways, including the following. Setting a predefined baseline period at the beginning of the anesthesia and/or operation, or before the induction of anesthesia, to represent the reference value, and comparing the signal, e.g. PPG amplitude or vertical position of the dicrotic notch, to this baseline period e.g. by diving the current value of the signal by the mean of the reference period value, or by subtracting the current value from the mean of the reference period value, or by using some other comparable operation. Alternatively, using a moving baseline, i.e. computing a reference value for a signal as a mean or median of the signal over a long period, in this case e.g. a few minutes, and comparing the current value to this reference value. The current or prevailing value refers to a single heart beat and a parameter, e.g. PPG amplitude or notch position, derived from this single pulse. The outcome of the overall algorithm would typically compute a mean value over several current values, typically a number R of 20 to 40 beats.

In the third step a nociception and/or adequacy of analgesia is assessed, whereupon the relationship between the prevailing notch signal(s) and the calculated reference value is evaluated. The equalized and proportionated dicrotic notch signal value(s) having a lower value $-\Delta N$ than said reference value evidences presence of nociception in the patient, and the equalized and proportionated dicrotic notch signal value(s)

having a same or higher value +ΔN than said reference value evidences lack of nociception in the patient.

Finally the detected change of the shape in the pulse, e.g. the difference ΔN as a change is one pulse wave parameter, from the second step is displayed and/or recorded in a proper form, which can be utilized for evaluating an adequacy of analgesia in the patient. It shall be also understood that to the results from the evaluative third step can be displayed and/or recorded, too. Anyway the final conclusions concerning the measures necessary for the patient belong to the responsibilities of the physician or anesthesiologist.

The pulse wave parameters used in the method according to the invention include parameters describing shape of the said individual heart beat pulses. The preferred embodiment described utilizes signal level analysis and derivatives analysis, but the method of the invention is not limited to this kind of analysis. Curvature analysis—curvature is the derivative of the inclination of the tangent with respect to arc length, as known—can be utilized, as well as any other type of calculations guiding to respective result.

Figure 8:
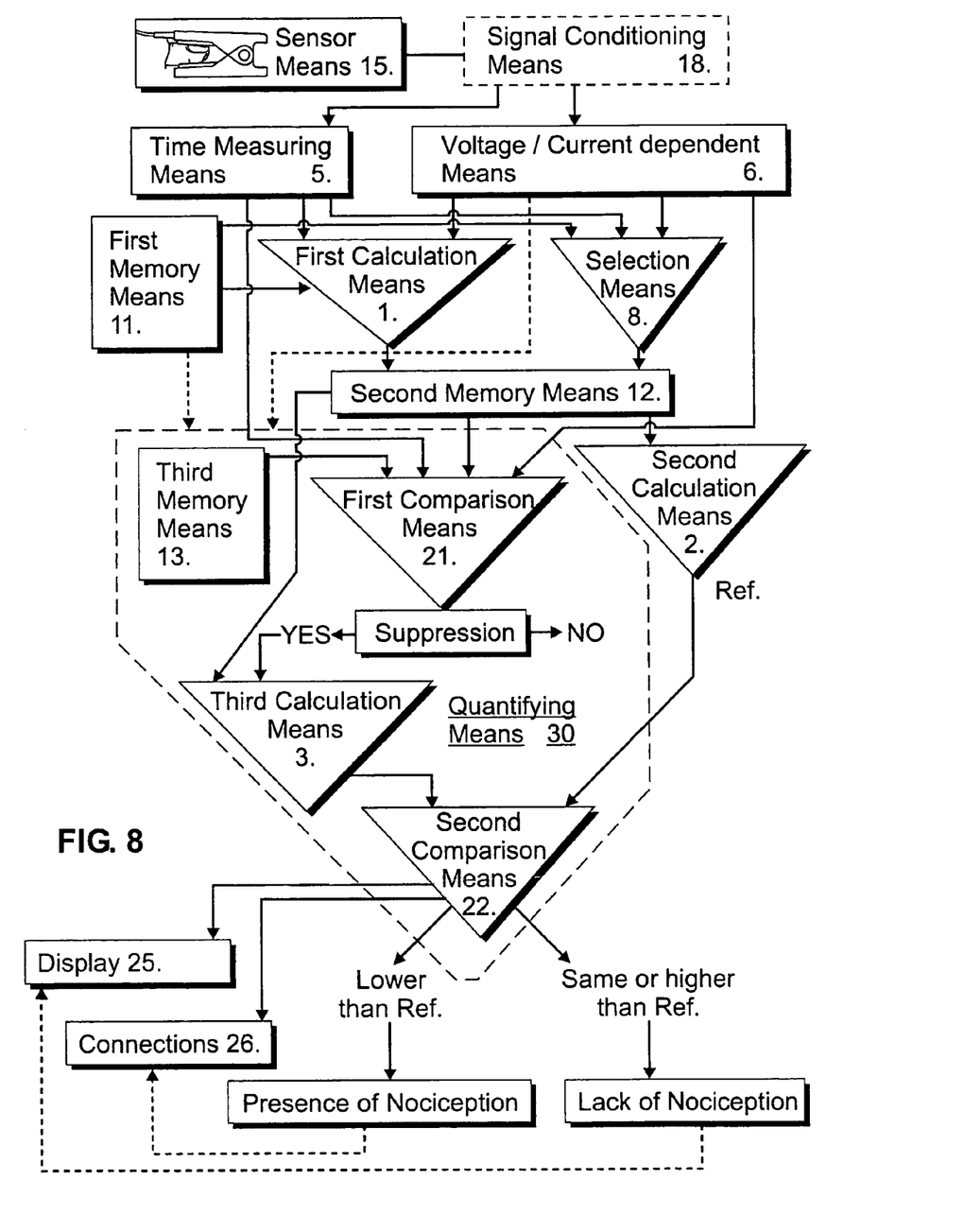
FIG. 8 shows the main components of the preferred embodiment of apparatus according to the invention as a flow chart. The components shown can be separate electronic units, but quite as well portions of a computer program or programs for microprocessors.
Figure 9A:
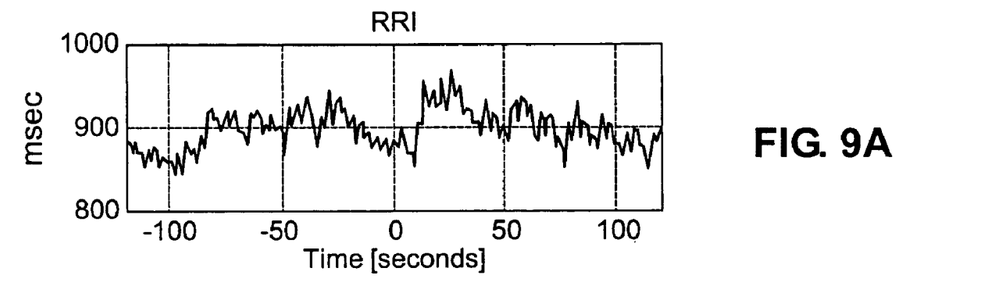
Figure 9B:
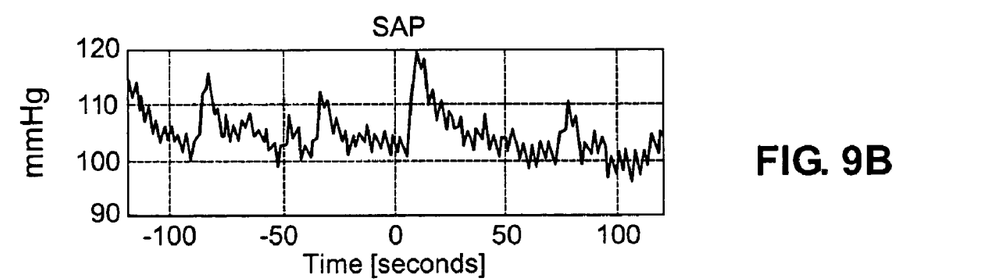
Figure 9C:
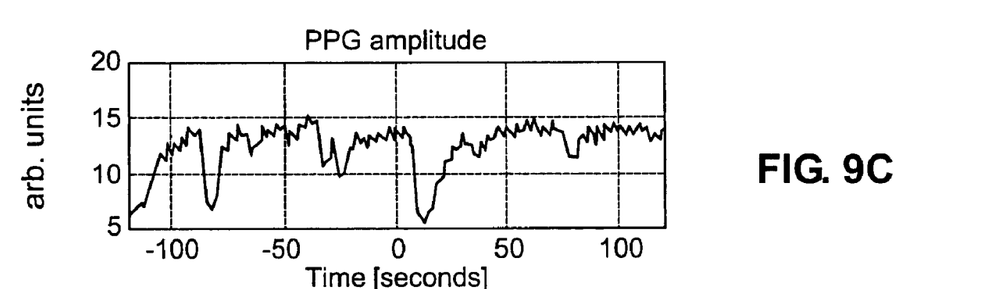
Figure 9D:
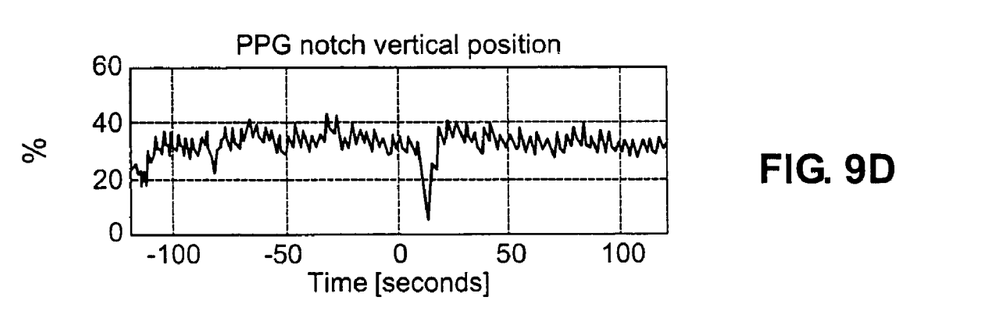

The apparatus for the described purpose comprises, as already mentioned, sensor means 15 for receiving a substantially continuous electrical signal S representing a cardiovascular flow of the patient, time measuring means 5 and a voltage/current dependent circuit 6, both connected with said sensor means, if necessary through a signal conditioning means 18. According to the invention the apparatus further comprises first memory means 11 storing criteria of predetermined pulse wave parameter(s) and first calculation means 1 and/or selection means 8 connected to said first memory means, said time measuring means and said voltage/current dependent circuit for detecting predefined pulse wave parameter(s) of said predetermined pulse wave parameter(s) in said signal. The measured and/or selected pulse wave parameter(s) are stored, at least temporarily, in the second memory means 12 connected to the selection means 8 and/or the first calculation means 1. The second calculation means 2 connected to the second memory means 12 provides then at least one reference value $y_{Ref}$ from a series of at least one predefined pulse wave parameter of said predetermined pulse wave parameters received prior to the present moment.

The apparatus also comprises quantifying means 30 providing quantified change(s) of at least one predefined pulse wave parameter in respect to values of said predefined pulse wave parameter prior to the present moment. The quantifying means 30 typically comprise third memory means 13 for storing threshold value for at least one of said predetermined pulse wave parameters, and the first comparison means 21, connected to said third memory means 13 and to said second memory means 12 as well as to the selection means 8 and/or the first calculation means 1, for detecting an exceeding or underrunning of said at least one predetermined pulse wave parameter as compared to said threshold value. The third calculation means 3, connected to the second memory means 12 and to the first comparison means 21, is provided for equalizing and proportionating at least predefined pulse wave parameter(s) of said predetermined pulse wave parameter(s). The second comparison means 22 for detecting a difference ΔN between prevailing value(s) of said at least one predefined pulse wave parameter and said at least one reference value is preferably included in the apparatus, too.

Finally there is a display 25 and/or connections 26 into other possible devices, whereupon at least said detected difference ΔN together with other necessary information and data is fed into the display or other device for utilization of the operator like physician.

It shall be understood that at least said quantifying means 30 can be a program for data processor, like those in computers, or separate electronic circuits as well. These kinds of programs and circuits are familiar to any person skilled in the art, and so they are not described in detail. The quantifying means 30 may operate either on the basis of signal levels analysis and derivatives analysis, as described in detail in the context of the method, but the quantifying means 30 may operate on the basis of curvatures analysis, too.

Said sensor means 15 is a photoplethysmographic unit, and a peripheral continuous blood pressure meter, or preferably a pulse oximeter. These kinds of sensors are widely known and commercially available, and so they are not described more in detail.

The present innovation covers different combinations of usage of PPG amplitude and notch position information, including:

PPG amplitude and PPG notch relative position may be detected and computed separately, and they may be normalized separately, and their information may be combined by a function working on the separately derived and normalized time series; and PPG notch amplitude may be derived by detecting the dicrotic notch from the PPG signal and computing its amplitude from the baseline signal, and this time series may be processed separately. The information in this signal combines the PPG amplitude information with the relative notch position.

The invention claimed is:

1. A method for monitoring a condition of a patient under anesthesia or sedation, the method comprising the steps of:
    acquiring a pulse wave signal representing peripheral cardiovascular flow in the patient;
    detecting individual heart beat pulses in said signal;
    measuring predetermined pulse wave parameters of said signal within said individual heart beat pulses;
    repeating the measuring of said pulse wave parameters in the successive heart beat pulses;
    recording said measured pulse wave parameters;
    calculating a reference value over a predetermined time period or over a predetermined number of heart beat pulses by deriving values of at least one predefined pulse wave parameter from said recorded pulse wave parameters;
    quantifying change(s) between one or several prevailing predefined pulse wave parameter(s) and said reference value; and
    displaying and/or recording said change(s) in said at least one pulse wave parameter.

2. A method according to claim 1, wherein said displaying and/or recording is in a form, which can be utilized for evaluating an adequacy of analgesia in the patient.

3. A method according to claim 1, wherein said predetermined pulse wave parameters are one or several parameter(s) selected from the following group of parameters: peak amplitude(s) within said individual heart beat pulse(s), and temporal position(s) of said pulse amplitude(s), and basal signal value(s) between said heart beat pulse(s), and dicrotic notch signal value(s) within said individual heart beat pulses, and temporal position(s) of said dicrotic notch value(s), and pulse area(s) of said heart beat pulse(s), and area(s) under curve(s) of said heart beat pulse(s).

4. A method according to claim 1, wherein said predefined pulse wave parameter is at least: dicrotic notch signal value(s) or virtual signal value(s) approaching dicrotic notch respectively, within successive heart beat pulses.

5. A method according to claim 1, the method further comprising, prior to said quantifying change(s), the step of:
- observing a possible suppression of any of said pulse wave parameters in their absolute value scale; and
- in case there is a suppression larger than a predetermined amount, deeming said quantified change(s) and/or optional evaluation and/or displaying and/or recording valid.

6. A method according to claim 3, the method further comprising, prior to said calculating change(s), the steps of:
- equalizing said pulse wave parameter(s) within pulse beat period(s); and
- proportionating said measured dicrotic notch signal value(s) and temporal position(s) thereof, and the calculated notch reference value(s) and temporal position(s) thereof to respect said equalized region of parameter(s) and period(s).

7. A method according to claim 6, the method further comprising the step of evaluation:
1) if the equalized and proportionated dicrotic notch signal value(s) has lower value than said reference value, evidencing presence of nociception in the patient,
2) if the equalized and proportionated dicrotic notch signal value(s) has a same or higher value than said reference value, evidencing lack of nociception in the patient.

8. A method according to claim 1, wherein said signal representing peripheral cardiovascular flow is a photoplethysmographic pulse wave signal, or a signal dependent on blood volume and/or a signal dependent on blood pressure.

9. A method according to claim 1, wherein said reference value is calculated specifically for the patient under anesthesia or sedation; and that said reference value is a constant average value over said time period or over said number of heart beat pulses prior to the present measuring time, or a moving weighted or non-weighted average value over said time period or over said number of heart beat pulses during operation of the patient, or a constant group average over certain patient type(s).

10. A method according to claim 1, wherein the recorded pulse wave parameters include parameters describing shape of the said individual heart beat pulses.

11. A method according to claim 1 or 10, wherein said signal representing peripheral cardiovascular flow is a photoplethysmographic wave obtained from a pulse oximeter.

12. A method according to claims 1, 2, 3, or 5, the method comprising:
- a first step, in which suppression of the wave parameters is detected;
- a second step, initiated after the first step if the suppression exceeds a certain second predetermined threshold value, in which step the change of the shape of the pulse is detected; and
- a third step, in which, based on the first and second steps, a nociception and/or adequacy of analgesia is assessed.

13. A method for monitoring a condition of a patient under anesthesia or sedation, the method comprising the steps of:
- acquiring a pulse wave signal representing peripheral cardiovascular flow in the patient;
- detecting successive heart beat pulses in said signal;
- measuring predetermined pulse wave parameters repeatedly in said signal within said successive heart beat pulses;
- comparing said predetermined pulse wave parameters in a number of successive heart beat pulses, and if a substantial alteration is occurred:
  - calculating a statistical reference value by deriving values from at least said predefined pulse wave parameters;
  - quantifying change(s) between at least one predefined pulse wave parameter and said reference value; and
- displaying and/or recording said change(s) or lack of change(s) respectively in said at least one predefined pulse wave parameter.

14. A method according to claim 13, wherein said displaying and/or recording is in a form, which can be utilized for evaluating an adequacy of analgesia in the patient.

15. A method according to claim 13, wherein said predetermined pulse wave parameters are one or several parameter(s) selected from the following group of parameters: peak amplitude(s) within said individual heart beat pulse(s), and temporal position(s) of said pulse amplitude(s), and basal signal value(s) between said heart beat pulse(s), and dicrotic notch signal value(s) within said individual heart beat pulses, and temporal position(s) of said dicrotic notch value(s), and pulse area(s) of said heart beat pulse(s), and area(s) under curve(s) of said heart beat pulse(s).

16. A method according to claim 13, wherein said predefined pulse wave parameter is at least: dicrotic notch signal value(s) or virtual signal value(s) approaching dicrotic notch respectively, within successive heart beat pulses.

17. A method according to claim 13, wherein the said substantial alteration is at least a suppression of the pulse amplitude(s) within said individual heart beat pulses compared in their absolute value scale.

18. A method according to claim 16, the method further comprising, prior to said calculating change(s), the steps of:
- equalizing said pulse wave parameter(s) within pulse beat period(s); and
- proportionating said measured dicrotic notch signal value(s) and temporal position(s) thereof, and the calculated notch reference value(s) and temporal position(s) thereof to respect said equalized region of parameter(s) and period(s).

19. A method according to claim 18, the method further comprising the step of evaluation:
1) if the equalized and proportionated dicrotic notch signal value(s) has a lower value than said reference value, evidencing presence of nociception in the patient,
2) if the equalized and proportionated dicrotic notch signal value(s) has a same or higher value than said reference value, evidencing lack of nociception in the patient.

20. A method according to claim 13, wherein said signal representing peripheral cardiovascular flow is a photoplethysmographic pulse wave signal, or a signal dependent on blood volume and/or a signal dependent on blood pressure.

21. A method according to claim 13, wherein said reference value is calculated specifically for the patient under anesthesia or sedation; and that said reference value is a constant average value calculated over a predetermined time period or over a predetermined number of heart beat pulses prior to the present measuring time, or a moving weighted or non-weighted average value over said time period or over said number of heart beat pulses during operation of the patient, or a constant group average over certain patient type(s).

22. A method according to claim 13, wherein the recorded pulse wave parameters include parameters describing shape of the said individual heart beat pulses.

23. A method according to claim 13 or 22, wherein said signal representing peripheral cardiovascular flow is a photoplethysmographic wave obtained from a pulse oximeter.

24. A method according to claims 13, 14, 15, or 17, said steps comprising:
  detecting the suppression of the wave parameters;
  if suppression exceeds a certain second predetermined threshold value, detecting the change in the shape of the heart beat pulse; and
  assessing a nociception and/or adequacy of analgesia if said suppression and said change in shape is detected.

25. An apparatus for monitoring a condition of a patient under anaesthesia or sedation, the apparatus comprising:
  a photoplethysmographic or a pulse oximeter sensor for receiving a substantially continuous electrical signal representing a cardiovascular flow of the patient;
  time measuring means and a voltage/current dependent circuit connected with said sensor means;
  first memory means storing criteria of predetermined pulse wave parameter(s);
  first calculation means and/or selection means connected to said first memory means, said voltage/current dependent circuit for detecting predefined pulse wave parameter(s) of said predetermined pulse wave parameter(s) in said signal;
  quantifying means providing quantified change(s) of at least one predefined pulse wave parameter in respect to values of said predefined pulse wave parameter prior to the present moment; and
  a display and/or connections into other possible devices.

26. An apparatus according to claim 25, the apparatus further comprising:
  second memory means for storing said measured and/or selected pulse wave parameter(s) at least temporarily; and
  second calculation means providing at least one reference value from a series of at least one predefined pulse wave parameter of said predetermined pulse wave parameters received prior to the present moment.

27. An apparatus according to claim 26, said quantifying means comprising:
  third memory means for storing threshold value for at least one of said predetermined pulse wave parameters; and
  first comparison means for detecting an exceeding or underrunning of said at least one predetermined pulse wave parameter as compared to said threshold value.

28. An apparatus according to claim 27, said quantifying means further comprising:
  third calculation means for equalizing and proportionating at least predefined pulse wave parameter(s) of said predetermined pulse wave parameter(s); and
  second comparison means for detecting a difference between prevailing value(s) of said at least one predefined pulse wave parameter and said at least one reference value.

29. An apparatus according to claim 25, wherein at least said quantifying means is a program for data processor.

30. An apparatus according to claim 25, wherein said quantifying means operates either on the basis of signal levels analysis and derivatives analysis, or on the basis of curvatures analysis.

31. An apparatus according to claim 25, wherein said sensor means is a photoplethysmographic unit.

32. An apparatus according to claim 31, wherein said sensor means is a pulse oximeter, or a peripheral continuous blood pressure meter.

* * * * *